(12) United States Patent
Cabri et al.

(10) Patent No.: US 10,577,433 B2
(45) Date of Patent: Mar. 3, 2020

(54) PROCESS FOR THE PREPARATION OF SUGAMMADEX

(71) Applicant: FRESENIUS KABI IPSUM S.R.L., Cassina de' Pecchi (Milan) (IT)

(72) Inventors: Walter Cabri, Milan (IT); Antonio Ricci, Pescara (IT); Jacopo Zanon, Venice (IT); Saswata Lahiri, Ghaziabad (IN); Govind Singh, Ghaziabad (IN); Shivaji Haribhau Shelke, Maharashtra (IN); Tapanjyoti Biswal, Haryana (IN); Nitin Kumar, Delhi (IN); Madan Singh, Delhi (IN)

(73) Assignee: Fresenius Kabi iPSUM S.r.l., Cassina de' Pecchi (Milan) (IT)

( * ) Notice: Subject to any disclaimer, the term of this patent is extended or adjusted under 35 U.S.C. 154(b) by 0 days.

(21) Appl. No.: 16/087,065

(22) PCT Filed: Mar. 20, 2017

(86) PCT No.: PCT/IB2017/051594
§ 371 (c)(1),
(2) Date: Sep. 20, 2018

(87) PCT Pub. No.: WO2017/163165
PCT Pub. Date: Sep. 28, 2017

(65) Prior Publication Data
US 2019/0284308 A1 Sep. 19, 2019

(30) Foreign Application Priority Data

Mar. 22, 2016 (IN) .............................. 201611009993

(51) Int. Cl.
| C08B 37/16 | (2006.01) |
| C07C 323/52 | (2006.01) |
| C07C 319/12 | (2006.01) |
| C08B 37/00 | (2006.01) |

(52) U.S. Cl.
CPC ........ *C08B 37/0012* (2013.01); *C07C 319/12* (2013.01); *C07C 323/52* (2013.01); *C08B 37/0003* (2013.01)

(58) Field of Classification Search
None
See application file for complete search history.

(56) References Cited

U.S. PATENT DOCUMENTS

| 2014/0221641 A1* | 8/2014 | Davuluri | ............. | C08B 37/0012 536/103 |
| 2018/0171033 A1 | 6/2018 | Alaparthi et al. | | |
| 2018/0346608 A1 | 12/2018 | Cabri et al. | | |
| 2018/0355070 A1 | 12/2018 | Cabri et al. | | |

FOREIGN PATENT DOCUMENTS

| CN | 101864003 A | 10/2010 |
| CN | 104844732 A2 | 8/2015 |
| CN | 105273095 A | 1/2016 |
| EP | 3 380 530 A1 | 10/2018 |
| EP | 3 380 554 A1 | 10/2018 |
| IN | 20161008861 | 3/2015 |
| IN | 2089/MUM/2015 | 5/2015 |
| IN | 3842/DEL/2015 | 11/2015 |
| IN | 3843/DEL/2015 | 11/2015 |
| WO | WO 2001/040316 A1 | 6/2001 |
| WO | WO 2012/025937 A1 | 3/2012 |
| WO | WO 2014/125501 A1 | 8/2014 |
| WO | WO 2016/194001 A1 | 8/2016 |
| WO | WO 2017/089966 A1 | 6/2017 |
| WO | WO 2017/089978 A1 | 6/2017 |

OTHER PUBLICATIONS

European Patent Office, Third Party Observation filed in European Patent Application No. 17720572.1 (May 29, 2019).
U.S. Appl. No. 15/779,038, filed May 24, 2018.
U.S. Appl. No. 15/779,040, filed May 24, 2018.
Comparison Report—Comparison of the procedures as disclosed in Example 3 of WO 2001/040316 A1, Example 1 of WO 2012/025937 A1, and Example 1 of WO 2014/125501 A1, and as reported in European Patent Application No. 16822742.9 (dated Feb. 1, 2019).
Comparison Report—Comparison of the procedures as disclosed in Example 3 of WO 2001/040316 A1, Example 1 of WO 2012/025937 A1, and Example 1 of WO 2014/125501 A1, and as reported in European Patent Application No. 16822270.1 (dated Feb. 1, 2019).
Experimental Report—Reproduction of examples 1 and 3-6 of the European Patent Application No. 16822742.9 (dated Feb. 1, 2019).
Experimental Report—Reproduction of examples 1-4 of the European Patent Application No. 16822270.1 (dated Feb. 1, 2019).
Guillo et al., "Synthesis of symmetrical cyclodextrin derivatives bearing multiple charges," *Bull. Soc. Chim. Fr.* 132(8): 857-866 (1995).
Liu et al., "A Convenient Procedure for the Formation of Per(6-deoxy-6-halo)cyclodextrins Using the Combination of Tetraethylammonium Halide with [Et$_2$NSF$_2$]BF$_4$," *Synthesis* 45(22): 3103-3105 (2013).
Okamatsu et al., "Design and evaluation of folate-appended α-, β-, and γ-cyclodextrins having a caproic acid as a tumor selective antitumor drug carrier in vitro and in vivo," *Biomacromolecules* 14(12): 4420-4428 (2013).
International Bureau of WIPO, International Preliminary Report on Patentability in International Application No. PCT/IB2016/057056 (dated May 29, 2018).

(Continued)

*Primary Examiner* — Layla D Berry
(74) *Attorney, Agent, or Firm* — Leydig, Voit & Mayer, Ltd.

(57) ABSTRACT

The present application provides an improved process for the preparation of sugammadex by reacting a salt of 3-mercapto propionic acid with 6-per-deoxy-6-per-halo-γ-cyclodextrin in a suitable organic solvent. This application also provides crystalline form of a salt of 3-mercapto propionic acid, preferably di sodium salt of 3-mercapto propionic acid and its use for the preparation of sugammadex, whereas formula (I) shows the sodium salt of sugammadex.

17 Claims, 1 Drawing Sheet

(56) References Cited

OTHER PUBLICATIONS

International Bureau of WIPO, International Preliminary Report on Patentability in International Application No. PCT/IB2016/057088 (dated May 29, 2018).
International Bureau of WIPO, International Preliminary Report on Patentability in International Application No. PCT/IB2017/051594 (dated Sep. 25, 2018).
European Patent Office, Third Party Observation filed in European Patent Application No. 16822742.9 (dated Feb. 14, 2019).
European Patent Office, Third Party Observation filed in European Patent Application No. 16822742.9 (Apr. 9, 2019).
European Patent Office, Third Party Observation filed in European Patent Application No. 16822270.1 (Feb. 14, 2019).
European Patent Office, Third Party Observation filed in European Patent Application No. 16822270.1 (Apr. 9, 2019).
European Patent Office, Third Party Observation filed in European Patent Application No. 17720572.1 (Mar. 19, 2019).
Chmurski et al., "An Improved Synthesis of 6-Deoxyhalo Cyclodextrins via Halomethylenemorpholinium Halides Vilsmeir-Haack Type Reagents," *Tetrahedron Letters* 38(42): 7365-7368 (1997).
European Medicines Agency, "Test Procedures and Acceptance Criteria for New Drug Substances and New Drug Products: Chemical Substances," Document CPMP/ICH/367/96 (2000) 32 pgs.
Hunt et al., "Structure and stability of columnar cyclomaltooctaose ($\gamma$-cyclodextrin) hydrate," *Carbohydrate Research* 340(9): 1631-1637 (2005).
European Patent Office, International Search Report in International Application No. PCT/IB2017/051594 (dated Jun. 7, 2017).
European Patent Office, Written Opinion in International Application No. PCT/IB2017/051594 (dated Jun. 7, 2017).
Chmurski et al., "An Improved Synthesis of Per(6-Deoxyhalo) Cyclodextrins Using N-Halosuccinimides-Triphenylphosphine in Dimethylformamide," *Supramolecular Chemistry*, vol. 12, pp. 221-224 (2000).
European Patent Office, Third Party Observation filed in European Patent Application No. 16822742.9 (Oct. 4, 2018).
European Patent Office, Third Party Observation filed in European Patent Application No. 16822270.1 (Oct. 7, 2018).

\* cited by examiner

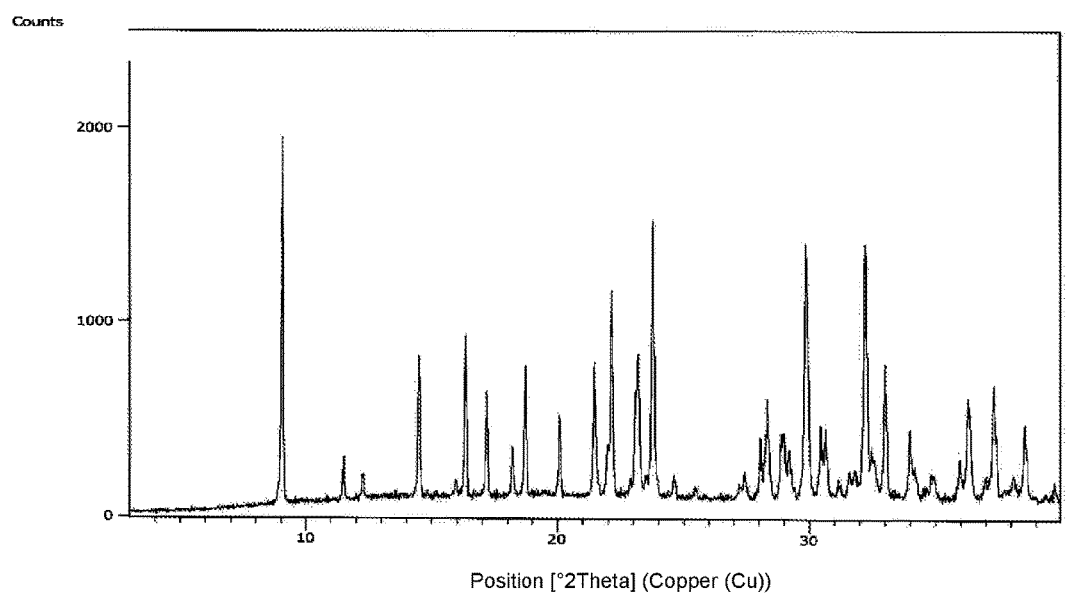

PROCESS FOR THE PREPARATION OF SUGAMMADEX

CROSS-REFERENCE TO RELATED APPLICATIONS

This patent application is the U.S. national stage of International Patent Application No. PCT/IB2017/051594, filed Mar. 20, 2017, which claims the benefit of Indian Patent Application No. IN201611009993, filed Mar. 22, 2016, the disclosures of which are incorporated herein by reference in their entireties for all purposes.

FIELD OF THE INVENTION

The present application provides an improved process for the preparation of sugammadex. More particularly, the application relates to a reaction of a salt of 3-mercapto propionic acid with 6-per-deoxy-6-per-chloro-γ-cyclodextrin to obtain sugammadex, wherein said salt is preferably selected from the group comprising of di sodium salt of 3-mercapto propionic acid, di potassium salt of 3-mercapto propionic acid and di lithium salt of 3-mercapto propionic acid. This application also relates to the use of isolated crystalline compound di alkali metal salt of 3-mercapto propionic acid for the preparation of sugammadex, which improves overall purity and/or reaction time of sugammadex.

The present application provides an improved industrially viable process, which is efficient, less time consuming, reproducible and involves less toxic reagents.

BACKGROUND OF THE INVENTION

Sugammadex is marketed as Bridion® and structurally known as compound of formula I, whereas formula I shows the sodium salt of sugammadex. It is an octa substituted γ-cyclodextrin derivative with a lipophilic core and a hydrophilic periphery.

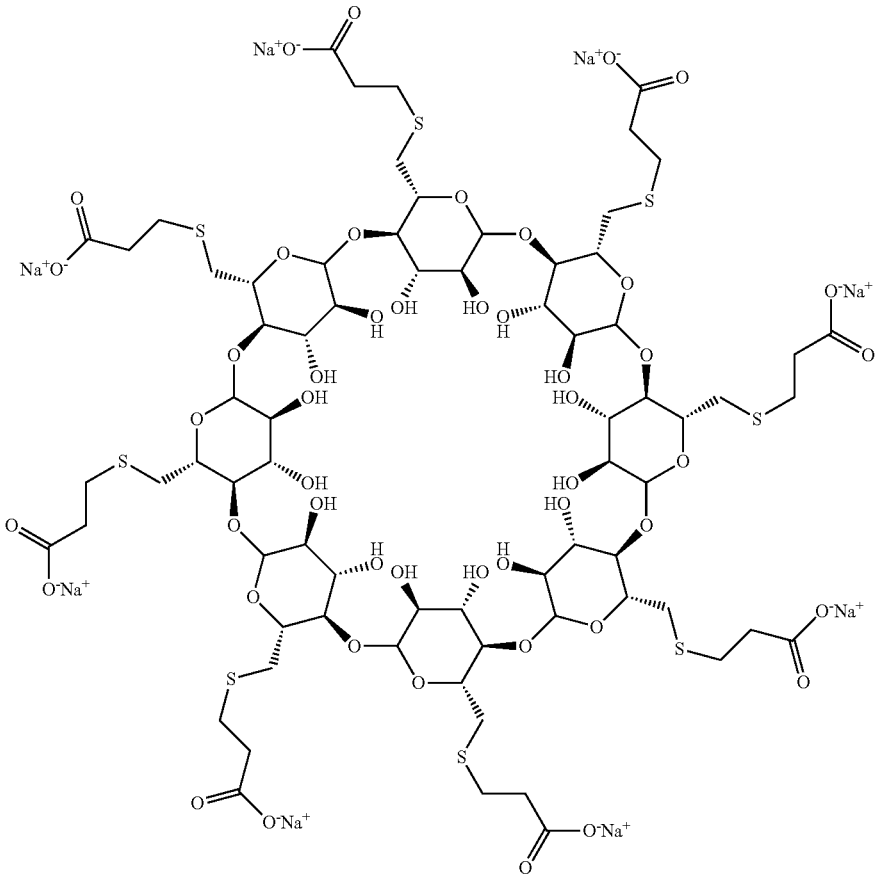

Formula I

The chemical structure of cyclodextrins (CD) contains a cyclic oligosaccharides composed of α-(1,4) linked glucopyranose subunits. According to the general accepted nomenclature of cyclodextrins, an α (alpha)-cyclodextrin is a 6-membered ring molecule, a β (beta)-cyclodextrin is a 7-membered ring molecule and a γ (gamma)-cyclodextrin is a 8-membered ring molecule. Cyclodextrins are useful molecular chelating agents. They possess a cage-like supramolecular structure. As a result of molecular complexation phenomena CDs are widely used in many industrial products, technologies and analytical methods.

Sugammadex contains substituted γ-cyclodextrin with eight recurring amylose units each with five asymmetric carbon atoms, in total forty asymmetric carbon atoms for the whole molecule. The original configuration of all asymmetric carbon atoms is retained during the synthetic manufacturing process.

According to various disclosures, including disclosures associated with Bridion®, suganimadex is a potent and effective agent for the reversal of neuromuscular blockade induced by the steroidal neuromuscular blocking agents (NMBA) such as rocuronium, vecuronium and pipecuronium.

Sugammadex was at least disclosed as early as the publication of WO2001/40316A1 (hereinafter referred as WO'316). This publication discloses a process for preparation of sugammadex which involves iodination of dry γ-cyclodextrin to obtain 6-per-deoxy-6-per-iodo-γ-cyclodextrin as a yellow solid. The 6-per-deoxy-6-per-iodo-γ-cyclodextrin was dissolved in dimethylformamide and added slowly to a mixture of 3-mercaptopropionic acid and sodium hydride in dry dimethylformamide. The obtained mixture was heated at 70° C. for 12 Hours. The mixture was cooled and water was added to the mixture. The volume of the mixture was reduced under vacuum by evaporation followed by addition of ethanol to precipitate sugammadex.

The process disclosed in WO2001/40316A1 suffers from the following disadvantages outlined below;

(i) The purity of sugammadex is low (about 88.75 area-% HPLC).

(ii) The use of pyrophoric sodium hydride is also not recommended as it forms explosive hydrogen gas, involves addition of mineral oil to the reaction mixture and is also associated with extensive foaming.

(iii) The process requires the distillation of high boiling point solvent such as water, which is time and energy consuming.

(iv) The reaction time of 6-per-deoxy-6-per-iodo-γ-cyclodextrin with 3-mercaptopropionic acid is also high (about 12 Hours).

WO2012/025937A1 (hereinafter referred as WO'937) discloses the preparation of sugammadex by chlorination of γ-cyclodextrin with phosphorous pentachloride in dimethylformamide, after completion of the chlorination the solvent was removed to obtain a viscous residue. The viscous residue was diluted with water followed by adjusting the pH 8 with 5M sodium hydroxide to obtain slurry, it was then filtered, washed with water and dried to give 6-per-deoxy-6-per-chloro-γ-cyclodextrin. The chlorinated γ-cyclodextrin was dissolved in dimethylformamide and added slowly to a mixture of 3-mercaptopropionic acid and sodium hydride in dimethylformamide. The obtained mixture was heated at 70-75° C. for 12 Hours. The dimethylformamide was partially removed then diluted with ethanol to obtain a precipitate. The precipitate is stirred for one hour and filtered to obtain crude sugammadex. The crude sugammadex was purified over silica gel and Sephadex G-25® column using water as eluent.

The process disclosed in WO2012/025937A1 suffers from the following disadvantages outlined below;

(i) The purity of sugammadex is about 94.35 area-% HPLC.

(ii) The procedure requires the utilization of chromatographic techniques for purification of the crude sugammadex, which are costly and hard to implement in the industrial production scale.

(iii) The use of pyrophoric sodium hydride is also not recommended as it forms explosive hydrogen gas, involves addition of mineral oil to the reaction mixture and is also associated with extensive foaming.

(iv) The process requires the distillation of high boiling point solvent such as dimethylformamide, which is time and energy consuming.

(v) The reaction time of 6-per-deoxy-6-per-chloro-γ-cyclodextrin with 3-mercaptopropionic acid is also high (about 12 Hours).

WO2014/125501A1 (hereinafter referred as WO'501) discloses the preparation of sugammadex by chlorination of γ-cyclodextrin with phosphorous pentachloride in dimethylformamide. After completion of the chlorination, the mixture was quenched with water. The obtained mixture was hydrolyzed with aqueous sodium hydroxide solution, filtered, washed repeatedly with water and dried to give 6-per-deoxy-6-per-chloro-γ-cyclodextrin. The chlorinated γ-cyclodextrin was added slowly to a mixture of 3-mercaptopropionic acid and sodium methoxide in methanol and dimethylformamide, then heated to 75-80° C. and maintained at 75-80° C. for 12 to 14 Hours to give crude sugammadex. The crude sugammadex was purified by treating it with activated carbon in a mixture of water and methanol.

The process disclosed in WO2014/125501A1 suffers from the following disadvantages outlined below;

(i) The purity of sugammadex is 88.50 area -% HPLC.

(ii) The reaction time of 6-per-deoxy-6-per-chloro-γ-cyclodextrin with 3-mercaptopropionic acid is also high (about 12 to 14 Hours).

CN104844732A2 discloses an alternative process for the preparation of sugammadex by reacting 6-per-deoxy-6-per-chloro-γ-cyclodextrin with thiourea in dimethylformamide at 90° C. for 12 Hours. After completion of the reaction, the solvent was partially evaporated followed by addition of ethanol to obtain a precipitate. The resulting solid precipitate was treated with aqueous sodium hydroxide solution followed by adjusting the pH 2 with hydrochloric acid. The ethanol was added to the mixture to obtain a solid residue, which was recrystallized in water to obtain 6-per-deoxy-6-per-mercapto-γ-cyclodextrin.

The 6-per-deoxy-6-per-mercapto-γ-cyclodextrin was reacted with acrylic acid in water under UV light exposure at 20° C. for 6 Hours. The pH of the solution was adjusted to 9 with aqueous sodium hydroxide solution followed by filtering the solution from nanofiltration membrane to obtain sugammadex.

The alternate process disclosed in CN104844732A2 involves specific techniques and instrument for the preparation of sugammadex, which are difficult to implement and control in the industrial scale.

Thus, the prior art procedures for the preparation of sugammadex suffers from the following disadvantages outlined below;

(i) The obtained purity of sugammadex is not satisfactory.

(ii) The reaction time of 6-per-deoxy-6-per-halo-γ-cyclodextrin with 3-mercaptopropionic acid is also very high and not suitable for large scale production.

(iii) The use of pyrophoric reagents such as sodium hydride is also not recommended as their handling is difficult at large scale production of sugammadex.

(iv) The use of special techniques such as chromatographic purification and utilization of UV light are difficult to implement and control in the industrial scale.

Finally, the longer time duration, handling of reagents, utilization of special. techniques and lower purity of sugammadex are not desirable for the preparation of sugammadex.

SUMMARY OF THE INVENTION

In one aspect, the application provides an improved process for the preparation of sugammadex, said process comprises the following steps;

a) reacting 6-per-deoxy-6-per-halo-γ-cyclodextrin of a compound of formula II,

Formula II

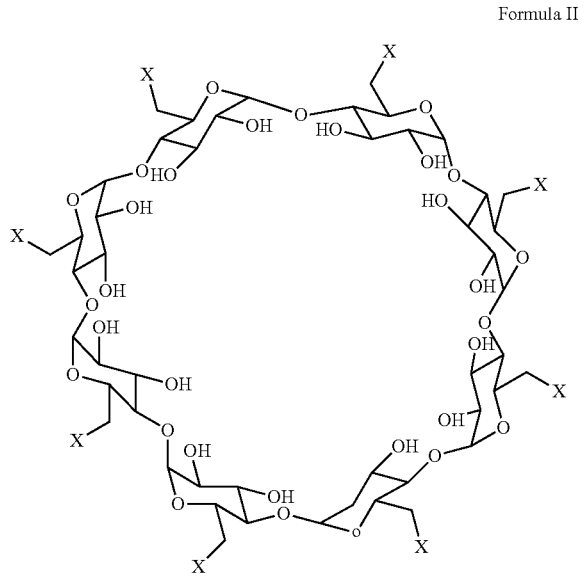

wherein, X is chlorine, bromine or iodine with a salt of 3-mercapto propionic acid, selected from the group comprising of di sodium salt of 3-mercapto propionic acid, di potassium salt of 3-mercapto propionic acid and di lithium salt of 3-mercapto propionic acid, preferably with the di sodium salt of 3-mercapto propionic acid of formula III, Formula III

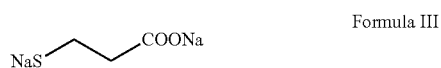

in suitable organic solvent to obtain sugammadex, b) optionally, purifying the sugammadex to obtain a sugammadex salt, preferably the sodium salt of formula I.

Formula I

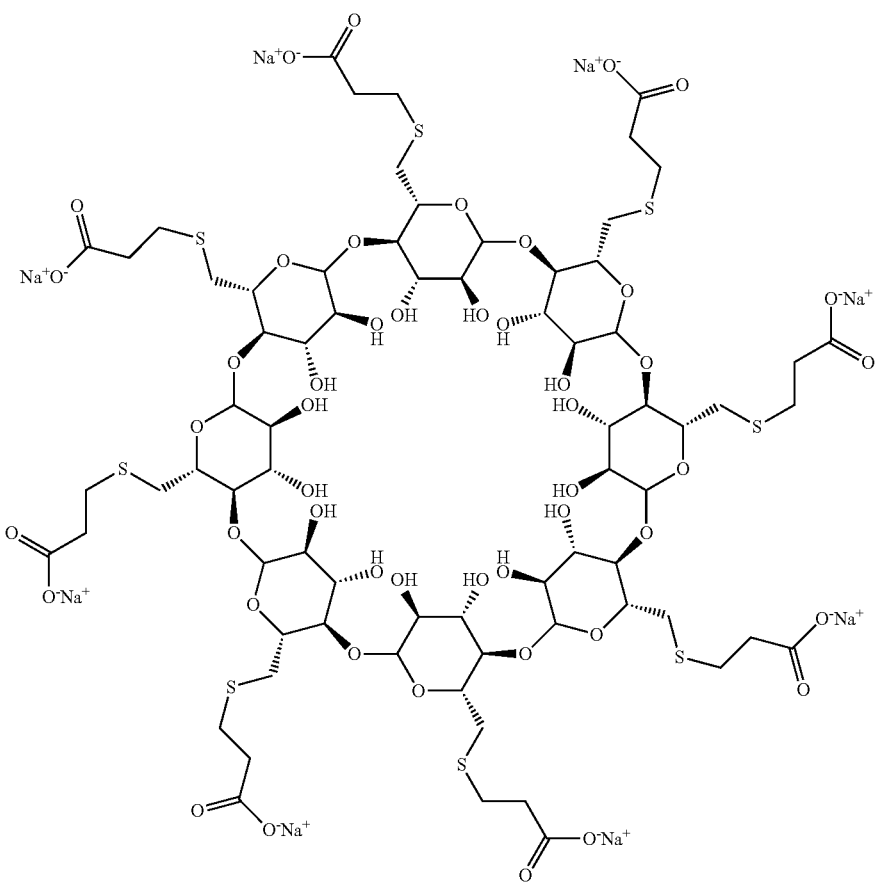

In another aspect, the application provides an improved process for the preparation and isolation of a salt of 3-mercapto propionic acid, selected from the group comprising of di sodium salt of 3-mercapto propionic acid, di potassium salt of 3-mercapto propionic acid and di lithium salt of 3-mercapto propionic acid, preferably the di sodium salt of 3-mercapto propionic acid of formula

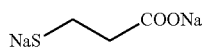

Formula III said process comprises the following steps, a) reacting a 3-mercaptopropionic acid with alkali metal hydroxide base in suitable organic solvent, wherein the alkali metal hydroxide base is selected from a group comprising of sodium hydroxide (NaOH), lithium hydroxide (LiOH) and potassium hydroxide (KOH), preferably with sodium hydroxide (NaOH), b) isolating the di alkali metal salt of 3-mercapto propionic acid, preferably the di sodium salt of 3-mercapto propionic acid, c) optionally, drying the di alkali metal salt of 3-mercapto propionic acid.

In yet another aspect, the application provides crystalline compound of a di alkali metal salt of 3-mercapto propionic acid, preferably the di sodium salt of 3-mercapto propionic acid of formula III,

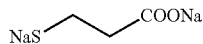

Formula III and its use for the preparation of sugammadex.

BRIEF DESCRIPTION OF THE DRAWING

The FIGURE is an illustration of a PXRD pattern of crystalline form of di sodium salt of 3-mercapto propionic acid.

DETAILED DESCRIPTION OF THE INVENTION

DEFINITIONS

The following definitions are used in connection with the present application unless the context indicates otherwise.

The terms alkali metal, alkali metal hydroxide and alkali metal salt refer to lithium (Li), sodium (Na) and/or potassium (K), its hydroxides and salts, respectively.

All percentages and ratios used herein are by weight of the total composition and all measurements made are at about 25° C. and about atmospheric pressure. All temperatures are in degrees Celsius.

The terms "about," "general," "generally" and the like are to be construed as modifying a term or value such that it is not an absolute. Such terms will be defined by the circumstances and the terms that they modify as those terms are understood by those of skill in the art. This includes, at the very least, the degree of expected experimental error, technique error and instrument error for a given technique used to measure a value.

As used herein, the terms "comprising" and "comprises" mean the elements recited, or their equivalents in structure or function, plus any other element or elements which are not recited.

The terms "having" and "including" are also to he construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

In general, polymorphism refers to the ability of a substance to exist as two or more crystalline phases that have different spatial arrangements and/or conformations of molecules in their crystal lattices. Thus, "polymorphs" refer to different crystalline forms of the same pure substance in which the molecules have different spatial arrangements of the molecules, atoms, and/or ions forming the crystal. Different polymorphs may have different physical properties such as melting points, solubilities, X-ray diffraction patterns, etc.

The term "anti-solvent" refers to a liquid that, when combined with a solution of sugammadex, reduces solubility of the sugammadex in the solution, causing crystallization or precipitation in some instances spontaneously, and in other instances with additional steps, such as seeding, cooling, scratching, and/or concentrating.

In one aspect, the application provides an improved process for the preparation of sugammadex by reacting 6-per-deoxy-6-per-halo-γ-cyclodextrin (halogenated-γ-cyclodextrin) with di alkali metal salt of 3-mercapto propionic acid in suitable organic solvent. The sugammadex may be further purified to get desired purity of sugammadex.

The improved process of the present application is advantageous over the prior art procedures at least because the reaction of halogenated-γ-cyclodextrin with isolated di alkali metal salt of 3-mercapto propionic acid is very selective, which in turn avoids the formation of unwanted impurities. Most preferred the halogen is chlorine and the alkali metal salt is of sodium, The prior art procedures disclose the preparation of a solution of 3-mercapto propionic acid in the presence of suitable base in a suitable solvent. The prepared solution containing large quantity of base, which is further mixed with 6-per-deoxy-6-per-halo-γ-cyclodextrin to afford sugammadex. It has been observed that the presence of excessive base during the substitution reaction of 6-per-deoxy-6-per-halo-γ-cyclodextrin with 3-mercapto propionic acid produces unwanted impurities, which are very difficult to remove from the reaction mixture.

The process of present application involves the preparation and isolation of di alkali metal salt of 3-mercapto propionic acid preferably the di sodium salt of 3-mercapto propionic acid as solid prior to its reaction with 6-per-deoxy-6-per-halo-γ-cyclodextrin. The use of isolated di sodium salt of 3-mercapto propionic acid for the reaction reduces the excessive content of base during the substitution reaction of 6-per-deoxy-6-per-halo-γ-cyclodextrin. It has been observed that impurities like Impurity I and Impurity II (Table A) are very susceptible to the quality and the choice of the base. in particular, Impurity I is directly correlated to the strength of the base used, while Impurity II is strictly correlated to the presence of sodium methoxide in the reaction medium. Moreover, the present process effectively reduces the presence of Impurity III (Table A) in the final sugammadex, which is currently present in the commercially available samples (Bridion) at a content of 4 area-% HPLC (High Performance Liquid Chromatography).

The content of impurity I is not detected in the samples of sugammadex prepared according to process of the present application, it is mainly due to isolation of di sodium salt of 3-mercapto propionic acid as solid. The isolation of solid intermediate significantly reduces the content of base during its reaction with 6-per-deoxy-6-per-halo-γ-cyclodextrin hence the formation of Impurity I is greatly reduced.

The removal of these impurities is also very difficult from the reaction mixture and even after multiple purifications these are not reduced to the acceptable limit in the final sugammadex.

Out of eight recurring amylose units of sugammadex one or more than one amylose unit is modified to form impurities of Table A.

The below comparative data discloses the content of three different impurities in the prepared sugammadex.

Preferably, the process of the present application is performed wider oxygen free condition to avoid the formation of oxidation sensitive impurities, The process of the present application is economical and effective for large scale production of sugammadex as the reaction time of 6-per-deoxy-6-per-halo-γ-cyclodextrin with 3-mercapto propionic acid is greatly reduced as compared to the prior art procedures. Further, it is observed that reaction mixture of the said substitution reaction of the present application is not viscous as compared to the prior art procedures. Due to low viscosity the handling and stirring of the reaction mixture is not tedious, which is useful for large scale production of sugammadex.

The comparative study with the prior art procedures for the reaction time and purity of the sugammadex are tabulated in table B.

TABLE A

| Impurity | WO'316 (Ref. Ex. 1) area-% HPLC | WO'937 (Ref. Ex. 2) area-% HPLC | WO'501 Ref. ex. 3) area-% HPLC | Examples of the present application area-% HPLC | | |
|---|---|---|---|---|---|---|
| | | | | Ex. 4C | Ex. 5 | Ex. 6 |
| 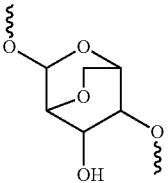 Intramolecular ether-SGX Impurity I | 0.24 | 1.84 | 0.38 | ND | ND | ND |
| 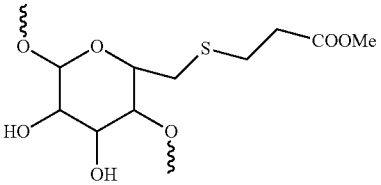 Methyl ester-SGX Impurity II | ND | ND | 0.74 | ND | ND | ND |
| 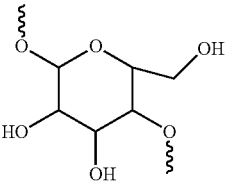 Hydroxy-SGX Impurity III | 1.20 | 1.45 | 1.57 | 0.45 | 0.24 | 0.37 |

SGX = Sugammadex;
ND = Not Detected

It is evident from the comparative data of Table A that high content of impurities are formed during the prior art procedures. Generally the product with high content of impurities is not accepted by pharmaceutical regulatory agencies for marketing. It is further observed that content of these impurities are not getting reduced, significantly, even after multiple purifications of crude sugammadex.

TABLE B

| Reference | Reaction time | Purity (area-% HPLC) |
|---|---|---|
| WO2001/040316A1 (Ref. Example 1) | 12 Hours | 88.75 |

TABLE B-continued

| Reference | Reaction time | Purity (area-% HPLC) |
|---|---|---|
| WO2012/025937A1 (Ref. Example 2) | 12 Hours | 94.35 |
| WO2014/125501A1 (Ref. Example 3) | 12-14 Hours | 88.50 |
| Example of the present application (Example 4C) | 4-5 Hours | 98.53 |
| Example of the present application (Example 5) | 4-5 Hours | 98.28 |
| Example of the present application (Example 6) | 4-6 Hours | 98.0 |

It is evident from the comparative data that process of present application requires lesser time for its completion and leads to higher purity of sugammadex.

According to the process of the present application, sugammadex is preferably prepared by reacting 6-per-deoxy-6-per-chloro-γ-cyclodextrin with isolated solid di sodium salt of 3-mercaptopropionic acid in suitable organic solvent. Said organic solvent can be selected form ethyl acetate, acetonitrile, propionitrile, tetrahydrofuran, dimethylformamide, dimethylacetamide, N-methyl-2-pyrrolidone, dimethyl sulfoxide or mixtures thereof. More preferably the organic solvent can be selected from dimethylformamide or dimethyl sulfoxide and most preferably the organic solvent is dimethyl sulfoxide.

The reaction can be carried out at any suitable temperature, but preferably from 40° C. to 90° C. or at the reflux temperature of the solvent. The reaction can be completed in about 2 to 6 Hours, more preferably in about 3 to 5 Hours.

Further, it is also advantageous to use dimethyl sulfoxide as reaction solvent in combination with the use of isolated solid di sodium salt of 3-mercaptopropionic acid, which accelerates the reaction leading to high substitutions in short reaction times and results in full substitutions of all eight halogenated positions of 6-per-deoxy-6-per-chloro-γ-cyclodextrin with 3-mercaptopropionic acid, more than 99% conversion is achieved by stirring the reaction mixture at 70° C. for about 2 to 6 Hours.

The completion of the reaction can be monitored by any suitable analytical technique. After completion of the reaction sugammadex may be isolated by any known methods which may include but not limited to cooling crystallization, anti-solvent addition, removal of solvent by evaporation, distillation, filtration of precipitated solid and the like; or any combinations of these methods.

The isolated sugammadex may optionally be purified to achieve desired. purity and quality by techniques known in art like column chromatography, fractional distillation, acid base treatment, slurrying or recrystallization. Preferably, the sugammadex can be purified by dissolving it in a suitable solvent like water followed by mixing with an anti solvent to isolate sugammadex. It is also advantageous to treat the mixture with activated carbon prior to addition of an anti solvent. The anti solvent can be selected from alcoholic solvent such as methanol, ethanol, isopropyl alcohol, acetone, tetrahydrofuran, dimethylformamide and dimethyl sulfoxide or mixtures thereof.

The purified sugammadex may be optionally washed with suitable solvent and dried under suitable drying conditions. The drying may be suitably carried out using any of an air tray dryer, vacuum tray dryer, fluidized bed dryer, spin flash dryer, flash dryer, and the like. The drying may be carried out at any suitable temperatures and under atmospheric pressure or above, or under reduced pressures.

In another aspect, the present application provides the preparation and isolation of di alkali metal salt of 3-mercapto propionic acid. The di alkali metal salt of 3-mercapto propionic acid may be prepared by reacting 3-mercapto propionic acid with suitable base preferably an alkali metal hydroxide base in suitable organic solvent and isolating the di alkali metal salt of 3-mercapto propionic acid as solid. The alkali metal hydroxide base can be selected from lithium hydroxide, potassium hydroxide, sodium hydroxide or mixtures thereof The most preferred alkali metal hydroxide base is sodium hydroxide and di alkali metal salt of 3-mercapto propionic acid is di sodium salt of 3-mercapto propionic acid. The preferred organic solvent can be selected from the list of organic solvent as discussed above. The most preferred organic solvent is tetrahydrofuran.

In still yet another aspect, the application provides novel crystalline compound of di sodium salt of 3-mercapto propionic acid of formula III,

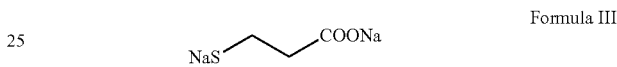

Formula III and its use for the preparation of sugammadex.

The crystalline di sodium salt of 3-mercapto propionic acid of formula III shows on X-ray diffraction peak at an angle of refraction 2 theta (θ), of 9.08, 22.14, 23.76, 29.82 and 32.2 degrees; preferably it includes five or more peaks at angles of refraction 2 theta (θ) selected from the group consisting of 9.08, 11.50, 12.24, 14.47, 15.95, 16.33, 17.17, 18.18, 18.70, 20.09, 21.45, 21.96, 22.14, 23.07, 23.19, 23.76, 24.60, 25,48, 27.20, 27.42, 28.02, 28.31, 28.86, 28.98, 29.16, 29.82, 29.92, 30.44, 30.64, 31.14, 31.58, 31.78, 32.20, 32.46, 32.59, 32.98, 33.08, 33,97, 34.81, 35.96, 36.27, 36.98, 37.32, 37.43, 38.11, 38,55 and 38.66±0.2 degrees.

The 6-per-deoxy-6-per-halo-γ-cyclodextrin of compound, used as starting material for the preparation of sugammadex of the present application, can be prepared by any suitable methods known in the prior arts such as methods disclosed WO2001/040316A1, WO2012/025937A1 and WO2014/125501A1. Generally, it can be prepared by halogenation of γ-cyclodextrin with a suitable halogenating reagent in a suitable organic solvent. The suitable halogenating reagent can be selected from iodine, N-iodosuccinimide, oxalyl chloride, oxalyl bromide, thionyl chloride, thionyl bromide, phosphoryl chloride or phosphoryl bromide; more preferably the halogenating reagent can be selected from oxalyl chloride or thionyl chloride. The organic solvent for the halogenation reaction can be selected from the list of organic solvent as discussed above. The most preferred organic solvent is dimethylformamide.

The halogenation of γ-cyclodextrin produces a complex with the halogenating reagent and solvent, which is further hydrolysed with a suitable base in a suitable solvent/anti-solvent mixture to isolate 6-per-deoxy-6-per-halo-γ-cyclodextrin. Preferably the anti-solvent is a mixture of alcoholic solvent and water. The solvent of solvent:anti-solvent pair can be selected from the list of organic solvents as discussed above. The alcoholic component of the anti-solvent can be selected from C1-4 alcohol such as methanol, ethanol, propanol, isopropyl alcohol, n-butanol, iso-butanol, tert-butanol or mixtures thereof. The suitable base can be selected from alkali metal hydroxide such as sodium hydroxide, lithium, hydroxide, potassium hydroxide and the like; alkali metal carbonate and/or alkali metal bicarbonate such as potassium carbonate, lithium carbonate, sodium carbonate, potassium bicarbonate, lithium bicarbonate, sodium bicarbonate and the like.

Preferably, the halogenation of γ-cyclodextrin is performed by reacting it with a suspension of oxalyl chloride or thionyl chloride in dimethylformamide under anhydrous condition at about −5° C. to 15° C., more preferably at about 0° C. to 10° C. The suspension of oxalyl chloride or thionyl chloride can be prepared by slow addition to dimethylformamide at about −5° C. to 15° C. The obtained suspension is further heated and mixed with γ-cyclodextrin. The mixing of γ-cyclodextrin with the suspension of oxalyl chloride or thionyl chloride can be achieved by addition of γ-cyclodextrin to the suspension or vice-versa, in both cases slow addition is preferred. After mixing, the obtained mixture may be stirred at a temperature of about 40° C. to 90° C., more preferably at about 60° C. to 80° C. for a period of about 5 to 25 Hours, preferably for about 10 to 20 Hours.

After completion of the reaction the solution is cooled and an alcoholic solvent, preferably methanol, is added then stirred for a period of time. The obtained solution is slowly added to an aqueous solution of base and methanol and then stirred for an appropriate time preferably for about 1 to 6 Hours, more preferably for about 1 to 4 Hours. The 6-per-deoxy-6-per-chloro-γ-cyclodextrin can be isolated from the reaction mixture by suitable techniques such as filtration, decantation or centrifugation and the like. The isolated 6-per-deoxy-6-per-chloro-γ-cyclodextrin may optionally be washed with aqueous methanol and if required, may optionally be further purified to obtain the desired purity of 6-per-deoxy-6-per-chloro-γ-cyclodextrin.

One embodiment of the process for preparing sugammadex comprises the following steps;
1) reacting 6-per-deoxy-6-per-chloro-γ-cyclodextrin of formula V,

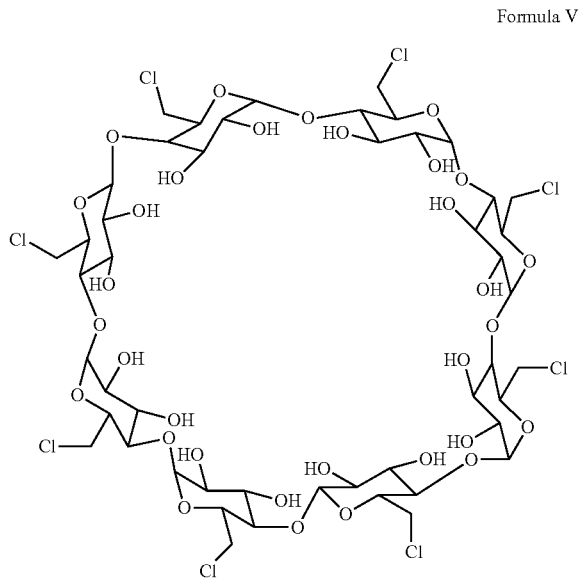 [SMILES: OC1C2OC(CCl)C(OC3OC(CCl)C(OC4OC(CCl)C(OC5OC(CCl)C(OC6OC(CCl)C(OC7OC(CCl)C(OC8OC(CCl)C(OC9OC(CCl)C(O2)C(O)C9O)C(O)C8O)C(O)C7O)C(O)C6O)C(O)C5O)C(O)C4O)C(O)C3O)C1O]

Formula V with isolated di sodium salt of 3-mercapto propionic acid of formula III,

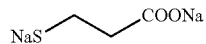

Formula III in dimethyl sulfoxide to obtain sugammadex,
2) dissolving sugammadex in water,
3) mixing with dimethyl sulfoxide,
4) stirring,
5) isolating sugammadex,
6) dissolving sugammadex of step 5) in water,
7) optionally, adding activated carbon,
8) mixing with methanol,
9) stirring,
10) isolating pure sugammadex.

Certain specific aspects of the present application will be explained in greater detail with reference to the following examples, which are provided only for purposes of illustration and should not be construed as limiting the scope of the disclosure in any manner.

EXAMPLES

To demonstrate the benefits of the present invention, example of the prior art were worked and indicated as reference example.

Reference Example 1 (Example 4 of WO2001/040316A1)

Preparation of Sugammadex

3-Mercapto propionic acid (1.95 mL, 10 eq,) was dissolved in dry dimethylformamide (72 mL) under nitrogen at room temperature. To this solution was added in three portions sodium hydride (1.97 g, 22 eq., 60% dispersion in mineral oil) and the mixture was stirred for another 30 minutes. To this mixture was then added drop wise a solution of 6-per-deoxy-6-per-iodo-γ-cyclodextrin (5 g, 2.24 mmol) in dry dimethylformamide (72 mL). After addition, the reaction mixture was heated at 70° C. for 12 Hours. After cooling, water (16 mL) was added to the mixture and the volume was reduced to 64 mL in vacuo. Ethanol (400 mL) was added resulting in precipitation. The solid precipitate was collected by filtration and dialyzed for 36 Hours. The volume was then reduced to 32 mL in vacuo. To this ethanol was added, and the precipitate was collected by filtration and dried to give the sugammadex as a white solid (2.1 g, 42% by wt) with a purity of 88.75 area-% HPLC.

Reference Example 2 (Example 2 of WO2012/025937A1)

Preparation of Sugammadex

To a mixture of sodium hydride (60% dispersion in mineral oil, 3.13 g) in dimethylformamide (19 mL, 3.8 vol.), a solution of 3-mercapto propionic acid (3 mL, 10 eq.) in dimethylformamide (6 mL, 1.2 vol.) was added slowly under nitrogen maintaining the temperature below 10° C. The resulting mixture was stirred at 20-25° C. for 30 minutes. Then 6-per-deoxy-6-per-chloro-γ-cyclodextrin (5 g) in dimethylformamide (50 mL, 10 vol.) was added slowly at 5-10° C. under nitrogen and the resulting mixture was heated to 70-75° C. for 12 Hours. Reaction mixture was cooled to 20-25° C. and dimethylformamide removed partially under vacuum and the reaction mixture is diluted with ethanol (75 mL, 15 vol.). The resulting precipitate was stirred at 20-25° C. for 1 Hour and filtered, washed with ethanol (10 mL, 2 vol.) and dried under vacuum at 60-65° C. The 9.4 g of ivory colored solid were obtained with a purity of 47.9 area-% HPLC. The crude product was purified over Silica Gel column and Sephadex G-25 column to afford 3.5 g of purified sugammadex with a purity of 94.35 area-% HPLC.

Reference Example 3 (Example 2 of WO2014/125501A1)

Preparation of Sugammadex

To a mixture of 4.5 mL (15 eq.) 3-mercapto propionic acid and 40 mL (8 vol.) dimethylformamide, a 30% solution of sodium methoxide (19 mL, 30 eq.) in methanol was added at 20-25° C. and stirred for 1 Hour at the same temperature. The compound 6-per-deoxy-6-per-chloro-γ-cyclodextrin (5 g) was added to the reaction mixture at 20-25° C. and heated to 75-80° C. for 12 to 14 Hours. After completion of the reaction, the reaction mixture was cooled to 20-25° C., then methanol (50 mL, 10 vol.) was added to the reaction mixture and stirred for 2 Hours at the same temperature. The resultant solid was filtered, washed with methanol (10 mL, 2 vol.) and dried under vacuum at 60-65° C. for 8 Hours.

The crude product (11.4 g) was dissolved in water (17 mL, 1.5 vol.) and methanol (17 mL, 1.5 vol.), treated with activated carbon (2.28 g, 20% w/w) and was filtered, washed the carbon cake with purified water (5 mL, 1 vol.). The filtrate was heated to 50-55° C. and slowly methanol (130 mL) was added at the same temperature in 1 Hour. The resulted suspension was cooled to 20-25° C. and stirred for 2 Hours at the same temperature. The resulted solid was filtered, washed with methanol (10 mL, 2 vol.) and dried under vacuum at 60-65° C. for 14 Hours to obtain 4.9 g of white solid with a purity of 88.5% area-% HPLC.

Example 1

Preparation of 6-Per-Deoxy-6-Per-Chloro-γ-Cyclodextrin (Reaction mass-1): Dimethylformamide (900 mL) was added to a reaction flask. The reaction mass was cooled to 0-10° C. and oxalyl chloride (distilled) (318 mL, 32 eq.) added by maintaining temperature at 0-10° C. After complete addition, the reaction mass was heated to 60-65° C. The γ-cyclodextrin (150 gm dissolved in 300 mL dimethylformamide) was added slowly into the reaction mass by maintaining the temperature at 60-65° C. After complete γ-cyclodextrin addition, reaction mass was stirred at 60-65° C. for 15 Hours. Then the reaction mass was cooled to 20-25° C. and methanol (1200 mL) was added and the reaction mass was stirred for another 5-10 minutes at 20-30° C.

(Reaction mass-2): Water (2700 mL) and potassium bicarbonate (463 gm) were mixed and stirred for 10-15 minutes at 20-30° C. Methanol (1500 mL) was added to the stirred solution and again stirred for 20-30 minutes at 20-30° C.

The reaction mass-1 was added slowly to the reaction mass-2 at 20-30° C. Addition was completed in 2-3 Hours at 20-30° C. The reaction mass was further stirred for 5-6 Hours at 20-30° C. After completion of the reaction, the reaction mass was filtered and the obtained solid was washed with methanol: water (1:1) (two times with 750 mL).

Then the solid was washed with methanol (750 mL) and dried for 30 minutes to obtain the crude compound 160 g.

Example 2

Preparation of 6-Per-Deoxy-6-Per-Chloro-γ-Cyclodextrin

A solution of crude 6-per-deoxy-6-per-chloromcyclodextrin (160 gm) of Example 1 in dimethylformamide (800 mL) was prepared and a mixture of t-Butanol: water (1:1) (400 mL) was added at 20-30° C. The reaction mass was stirred for 1 Hour. Then a mixture of t-Butanol: water (1:1) (400 mL) was added at 20-30° C. The reaction mass was stirred for 1 Hour at 20-30° C. and then cooled to 0-10° C. The reaction mass was further stirred for 2 Hours at 0-10° C. The reaction mass was filtered and the obtained solid was washed with t-Butanol: water (1:1) (two times with 320 mL). Finally the material was suck dried for 1 Hour and then dried under vacuum at 50-55° C. for 15 Hours to give pure 6-per-deoxy-6-per-chloro-γ-cyclodextrin (M/C=1-2%); $^1$H NMR (400 MHz, DMSO-d6) δ=5.96-5.98 (d, J=7.2 Hz, 8 H), 5.93 (s, 8H), 4.98-4.99 (d, J=3.2 Hz, 8H), 4.01-4.03 (d, J=9.6 Hz, 8 H), 3.81-3.84 (m, 16 H), 3.58-3.62 (m, 8H), 3.31-3.42 (m, 16 H). The product had a purity of 97.33 area-% HPLC.

Example 3

Preparation of Di-Sodium Salt of 3-Mercaptopropionic Acid

3-Mercaptopropionic acid (50 g, 0.47 moles) was added to tetrahydrofuran (500 ml) under nitrogen atmosphere and the reaction mixture was cooled to 5-10° C. A solution of sodium hydroxide (37.68 g, 0.94 moles) dissolved in 50 ml of water was added and the reaction mixture was stirred for 1 hour at 15-20° C. Dimethylformamide (250 mL) was added to the reaction mixture at 15-20° C. and the reaction mixture was stirred for 1 hour at 15-20° C. The suspension was filtered and washed with tetrahydrofuran:dimethylformamide (1:1) (200 ml).

The wet solid was stirred in tetrahydrofuran (500 ml) and dimethylformamide (250 ml) at 20 to 25° C. for 1 hour under nitrogen atmosphere. The suspension was filtered, washed with tetrahydrofuran:dimethylformamide (1:1) (200 ml) and dried under vacuum at 45-50° C. for 15 Hours to give 72 g of disodium salt of 3-mercaptopropionic acid. The obtained product had a purity of 97 area-% HPLC. $^1$H NMR (400 MHz, D$_2$O): δ 2.36-2.41 (m, 4H); δ 2.63-2.67 (m, 4H).

Example 4

Preparation of Sugammadex

Example 4A: Dimethyl sulfoxide (500 ml) was de-oxygenated with three cycles of nitrogen, vacuum and nitrogen at 20-30° C. The di-sodium salt of 3-mercaptopropionic acid (46 g, 0.306 moles) was added and the reaction mass was again de-oxygenated with two cycles of nitrogen and vacuum at 20-25° C. The 6-per-deoxy-6-per-chloro-γ-cyclodextrin (25 g, 0.017 moles) was dissolved, in dimethyl sulfoxide (100 ml) under nitrogen at 20-30° C. and added to the reaction mass at 20-25° C. Then the reaction mixture was de-oxygenated with four cycles of vacuum and nitrogen at 20-30° C. The reaction mixture was heated to 70-75° C. and stirred for 4-5 hour at 70-75° C. After completion of the reaction, the reaction mass was slowly cooled to 20-30° C., then filtered under nitrogen, washed with dimethyl sulfoxide (100 ml), ethanol (750 ml) and dried under vacuum at 40-50° C. for 15 Hours to give 43.7 g crude sugammadex.
$^1$H NMR (400 MHz, D$_2$O): δ 2.53-2.60 (m, 16H); δ 2.89-2.93 (t, 16H); δ 3.02-3.07 (m, 8H); δ 3.16-3.19 (d, 8H); δ 3.67-3.73 (m, 16H); δ 3.98-4.03 (t, 8H); δ 4.10-4.13 (m, 8H); δ 5.24-5.25 (d, 8H).

Example 4B: The crude sugammadex (43 g) was added to 180 ml of water at 20-30° C. and the mixture was stirred for 10-20 minutes at the same temperature to get a clear solution. Dimethyl sulfoxide (205 ml) was slowly added to the reaction mixture at 25-35° C. and the reaction mixture was then stirred at 20-30° C. for 1 hour. Further Dimethyl sulfoxide (65 mL) was added and the reaction mixture stirred for 1 hour at same temperature. The resultant solid was filtered, washed with 10% aqueous dimethyl sulfoxide (100 ml), ethanol (300 ml) and dried at 50-55° C. for 12 hour to give 28.10 g sugammadex.

Example 4C: The sugammadex (28 g) obtained from example 4B was dissolved in water (380 ml) and methanol (380 ml) at 20-30° C. To this solution activated carbon (2.8 g, 10% w/w) was added and stirred for 2 Hours at 20-30° C. The reaction mixture was filtered through celite and washed with methanol:water (1:1) (38 ml). The filtered solution was heated to 45-50° C. and methanol (2400 ml) was slowly added at the same temperature. The reaction mixture was then slowly cooled to 20-30° C. and stirred at the same temperature for 1 Hour. The reaction mass was filtered, washed with methanol (100 ml) and dried under vacuum at 60-65° C. for 15 Hours to give 24 g of sugammadex. The product had purity of 98.53 area-% HPLC, Impurity I=Not Detected, Impurity II=Not Detected, Impurity III=0.45.

Example 5

Preparation of Sugammadex

Dimethyl sulfoxide (200 ml) was de-oxygenated with nitrogen, vacuum and nitrogen at 20-30° C. The di-sodium salt of 3-mercaptopropionic acid (16.6 g, 0.1107 moles) was added and the reaction mass was again de-oxygenated with nitrogen and vacuum at 20-25° C. The 6-per-deoxy-6-per-chloro-γ-cyclodextrin (10 g, 0.0069 moles) was dissolved in dimethyl sulfoxide (50 ml) under nitrogen at 20-30° C. and added to the reaction mass at 20-25° C. Then the reaction mixture was de-oxygenated with vacuum and nitrogen at 20-30° C. The reaction mixture was heated to 70-75° C. and stirred for 4-5 hour at 70-75° C. The reaction mass was cooled to 20-30° C. and diluted with water (250 ml) at 20-35° C. Slowly added dimethyl sulfoxide (180 ml) to the reaction mass in two lots at 20-35° C. and stirred for 1 hour at 20-30° C., then filtered the mass under nitrogen, washed with 20% water in dimethyl sulfoxide (40 ml), suck dried under vacuum 1-2 hours to give Sugammadex with purity 98.28%, Impurity I=Not Detected, Impurity II=Not Detected, Impurity III=0.24.
$^1$H NMR (400 MHz, D$_2$O): δ 2.53-2.60 (m, 16H); δ 2.89-2.93 (t, 16H); δ 3.02-3.07 (m, 8H); δ 3.16-3.19 (d, 8H); δ 3.67-3.73 (m, 16H); δ 3.98-4.03 (t, 8H); δ 4.10-4.13 (m, 8H); δ 5.24-5.25 (d, 8H).

Example 6

Preparation of Sugammadex

Dimethyl sulfoxide (2000 ml) was de-oxygenated with nitrogen, vacuum and nitrogen at 20-30° C., The di-sodium salt of 3-mercaptopropionic acid (166.2 g, 1.107 moles) was added and the reaction mass was again de-oxygenated with nitrogen and vacuum at 20-25° C. The 6-per-deoxy-6-per-chloro-γ-cyclodextrin (100 g, 0.069 moles) was dissolved, in dimethyl sulfoxide (500 ml) under nitrogen at 20-30° C. and added to the reaction mass at 20-25° C. Then the reaction mixture was de-oxygenated with vacuum and nitrogen at 20-30° C. The reaction mixture was heated to 70-75° C. and stirred for 4-6 hour at 70-75° C. The reaction mass was cooled to 20-30° C. and diluted with water (2500 ml) at 20-35° C. Slowly added dimethyl sulfoxide (1800 ml) to the reaction mass in two lots at 20-35° C. and stirred for overnight at 20-30° C., then filtered the mass under nitrogen, washed with 20% aqueous dimethyl sulfoxide (400 ml), suck dried under vacuum 1-2 hours to give 220 gm Sugammadex.

The obtained Sugammadex was dissolved in 800 ml of water. Dimethyl sulfoxide (1600 ml) was slowly added to the reaction mixture at 25-35° C. in two lots and the mass was stirred for 3 hour at 20-30° C. The mass was filtered and washed with 20% aqueous dimethyl sulfoxide (400 ml), methanol (500 ml) and suck dried under nitrogen for 1 hour to give 100 g wet Sugammadex.

The obtained solid was dissolved in water (500 ml). To this solution activated carbon (10 g) was added and stirred for 1-2 Hours at 20-30° C. The mass was filtered through 5 micron and then washed with water (300 ml). The filtered mass was diluted slowly by adding methanol (4800 ml) at 20-35° C. The mass was stirred at 20-30° C. for 5-6 Hours. The mass was filtered, washed with methanol (400 ml) and dried under vacuum at 55-65° C. for 12-15 hours to give 70 g of Sugammadex. The obtained Sugammadex (70 g) was dissolved in water (500 ml), treated with activated carbon and filtered through 0.45 micron, The filtrate was lyophilized to give 60 g of Sugammadex. The product had purity of 98.0 area-% HPLC, Impurity I=Not Detected, Impurity II=Not Detected, Impurity III=0.37.
$^1$H NMR (400 MHz, D$_2$O): δ 2.53-2.60 (m, 16H); δ 2.89-2.93 (t, 16H); δ 3.02-3.07 (m, 8H); δ 3.16-3.19 (d, 8H); δ 3.67-3.73 (m, 16H); δ 3.98-4.03 (t, 8H); δ 4.10-4.13 (m, 8H); δ 5.24-5.25 (d, 8H).

The invention claimed is:
1. A process for preparing sugammadex of formula I,

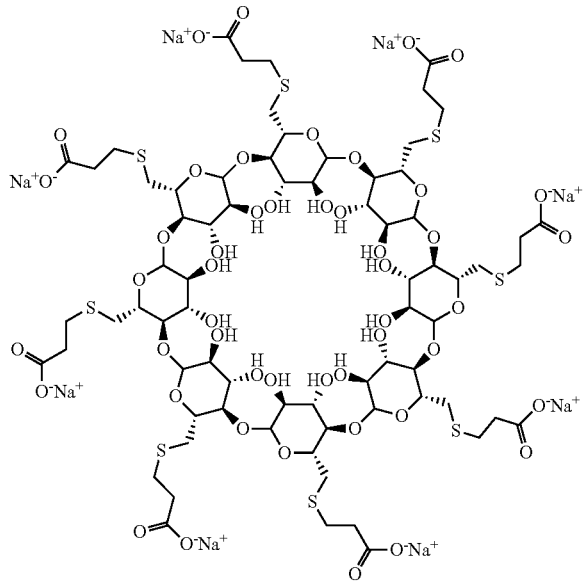

Formula I the process comprising,
a) reacting 6-per-deoxy-6-per-halo-γ-cyclodextrin of formula II, Formula II

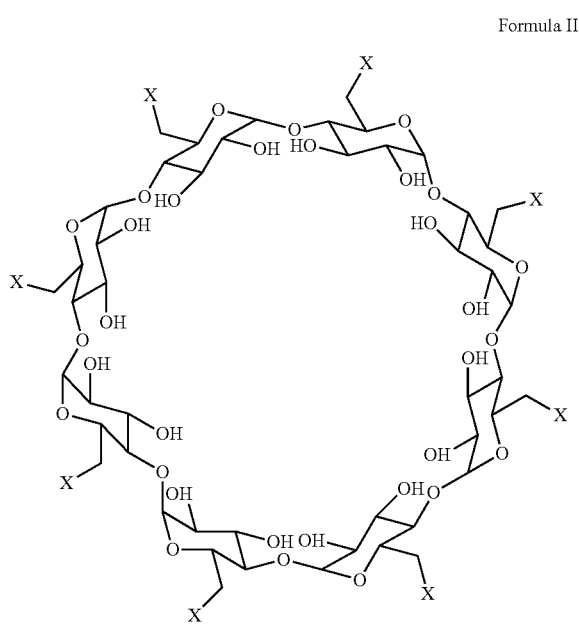

wherein, X is chlorine, bromine or iodine,
with a salt of 3-mercapto propionic acid, selected from di sodium salt of 3-mercapto propionic acid, di lithium salt of 3-mercapto propionic acid, and di potassium salt of 3-mercapto propionic acid, in an organic solvent to obtain sugammadex, wherein the salt is isolated, and
  b) optionally, purifying the sugammadex.

2. The process according to claim 1 wherein the 6-per-deoxy-6-per-halo-γ-cyclodextrin is prepared by a process that comprises,
  i) reacting γ-cyclodextrin of formula IV, Formula IV

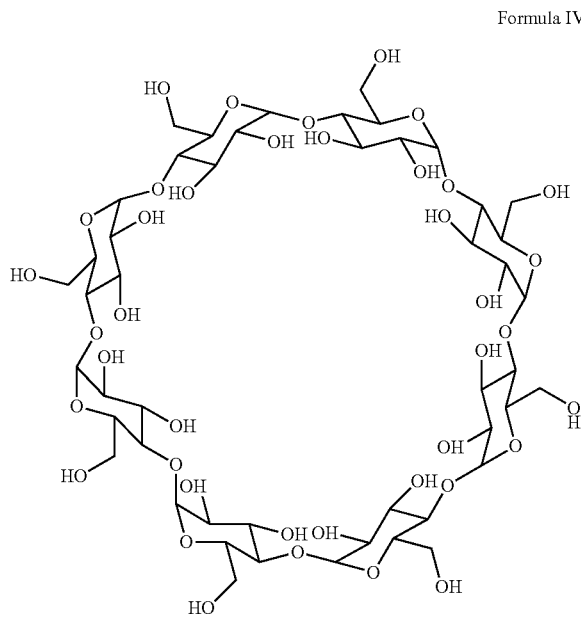 [SMILES: OCC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

with a halogenating agent, in an organic solvent,
  ii) adding to the reaction mixture of step i) an aqueous solution of base and alcoholic solvent, iii) isolating the 6-per-deoxy-6-per-halo-γ-cyclodextrin of formula II,
  iv) optionally, drying the 6-per-deoxy-6-per-halo-γ-cyclodextrin, and
  v) optionally, purifying the compound of step iii) or iv).

3. The process according to claim 1, wherein the salt of 3-mercapto propionic acid is the di sodium salt of 3-mercapto propionic acid.

4. The process according to claim 3, wherein the di sodium salt of 3-mercapto propionic acid is prepared by a process that comprises,
  i) reacting 3-mercaptopropionic acid with an alkali metal hydroxide base in an organic solvent, to produce the di sodium salt of 3-mercapto propionic acid,
  ii) isolating the di sodium salt of 3-mercapto propionic acid, and
  iii) optionally, drying the di sodium salt of 3-mercapto propionic acid.

5. The process according to claim 1, wherein the organic solvent is selected from ethyl acetate, acetonitrile, propionitrile, tetrahydrofuran, dimethylformamide, dimethylacetamide, N-methyl-2-pyrrolidone, dimethyl sulfoxide and mixtures thereof.

6. The process according to claim 2, wherein the halogenating agent is iodine, N-iodosuccinimide, oxalyl chloride, oxalyl bromide, thionyl chloride, thionyl bromide, phosphoryl chloride or phosphoryl bromide.

7. The process according to claim 2, wherein the base used in step ii) is selected from alkali metal hydroxides, alkali metal carbonates, alkali metal bicarbonates, and mixtures thereof.

8. The process according to claim 2, wherein the alcoholic solvent of step ii) is selected from methanol, ethanol, propanol, isopropyl alcohol, n-butanol, isobutanol, tert-butanol and mixtures thereof.

9. The process according to claim 4, wherein the alkali metal hydroxide base of step i) is selected from lithium hydroxide, potassium hydroxide, sodium hydroxide and mixtures thereof.

10. The process according to claim 1, wherein the di sodium salt of 3-mercapto propionic acid is isolated as a solid before its reaction with the 6-per-deoxy-6-per-halo-γ-cyclodextrin of formula II.

11. The process according to claim 1, comprising purifying sugammadex according to step b) by a process that comprises,
  b1) dissolving sugammadex in solvent,
  b2) optionally, adding activated carbon,
  b3) adding an anti solvent,
  b4) stirring, and
  b5) isolating purified sugammadex.

12. The process according to claim 11, wherein solvent of step b1) is water.

13. The process according to claim 11, wherein anti solvent of step b3) is selected from methanol, ethanol, isopropyl alcohol, acetone, tetrahydrofuran, dimethylformamide and dimethyl sulfoxide.

14. The process according to claim 1, wherein the organic solvent of step a) is dimethyl sulfoxide.

15. The process according to claim 1, comprising,
  1) reacting 6-per-deoxy-6-per-chloro-γ-cyclodextrin of formula V Formula V

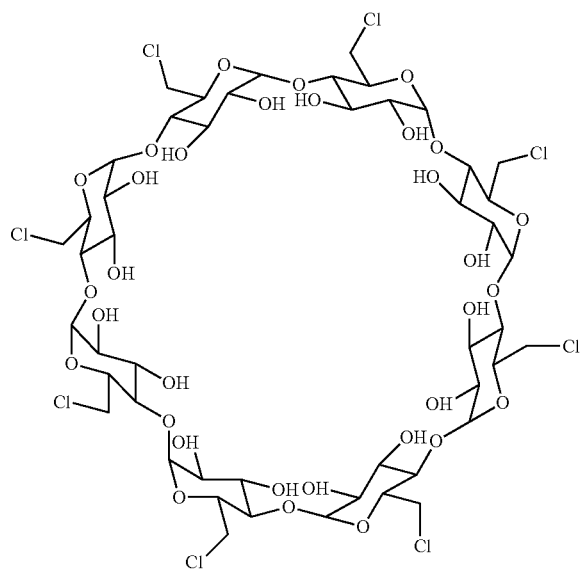

with the di sodium salt of 3-mercapto propionic acid in dimethyl sulfoxide to obtain crude sugammadex, 2) dissolving the crude sugammadex in water,
3) adding dimethyl sulfoxide,
4) stirring,
5) isolating sugammadex,
6) dissolving the sugammadex of step 5) in water,
7) optionally adding activated carbon,
8) adding methanol,
9) stirring, and
10) isolating purified sugammadex.

16. The process according to claim 10, wherein the di sodium salt of 3-mercapto propionic acid is crystalline and exhibits XRPD peaks at an angle of refraction 2 theta ($\theta$) of 9.08, 22.14, 23.76, 29.82 and 32.2±0.2 degrees.

17. The process of claim 7, wherein the base is selected from lithium hydroxide, potassium hydroxide, sodium hydroxide, sodium carbonate, lithium carbonate, potassium carbonate, sodium bicarbonate, potassium bicarbonate, lithium bicarbonate, and mixtures thereof.

* * * * *